United States Patent
Semmens (10) Patent No.: US 9,782,321 B1
(45) Date of Patent: Oct. 10, 2017

(54) LOWER BODY ELECTRICAL MUSCLE STIMULATION EXERCISE SYSTEMS

(71) Applicant: Thomas Semmens, Las Vegas, NV (US)

(72) Inventor: Thomas Semmens, Las Vegas, NV (US)

(*) Notice: Subject to any disclaimer, the term of this patent is extended or adjusted under 35 U.S.C. 154(b) by 0 days.

(21) Appl. No.: 15/212,734

(22) Filed: Jul. 18, 2016

Related U.S. Application Data (60) Provisional application No. 62/283,878, filed on Sep. 15, 2015.

(51) Int. Cl.
   *A61H 1/02* (2006.01)
   *A61N 1/04* (2006.01)
   *A61N 1/36* (2006.01)

(52) U.S. Cl.
   CPC ............. *A61H 1/0214* (2013.01); *A61H 1/02* (2013.01); *A61H 1/0237* (2013.01); *A61N 1/0456* (2013.01); *A61N 1/0492* (2013.01); *A61N 1/36003* (2013.01); *A61N 1/36014* (2013.01); *A61H 2205/10* (2013.01)

(58) Field of Classification Search
   CPC .......... A61H 1/00; A61H 1/02; A61H 1/0214; A61H 1/0237; A61H 1/024; A61H 1/0244; A61H 1/0255; A61H 1/0259; A61H 3/04; A61H 2003/043; A61H 39/002; A61H 2201/0138; A61H 2201/0149; A61H 2201/0157; A61H 2201/10; A61H 2201/12; A61H 2201/1215; A61H 2201/1418; A61H 2201/1633; A61H 2201/164; A61H 2203/0425; A61H 2203/0431; A61H 2205/10; A61N 1/0456; A61N 1/0492; A61N 1/36003; A61N 1/36014
   USPC ................. 601/5, 15, 21, 23, 24, 26, 33–36; 482/57, 60
   See application file for complete search history.

(56) References Cited

U.S. PATENT DOCUMENTS

| | | | |
|---|---|---|---|
| 4,724,842 A | 2/1988 | Charters | |
| 4,809,696 A * | 3/1989 | Laenger | A61N 1/36003 607/48 |
| 4,947,836 A | 8/1990 | Laenger | |
| 2004/0127954 A1* | 7/2004 | McDonald, III | A61H 39/002 607/48 |
| 2004/0172093 A1 | 9/2004 | Rummerfield | |
| 2007/0208392 A1* | 9/2007 | Kuschner | A61N 1/36003 607/48 |

(Continued)

*Primary Examiner* — Justine Yu
*Assistant Examiner* — Colin W Stuart
(74) *Attorney, Agent, or Firm* — Integrity Patent Group, PLC; Edwin Wold (57) ABSTRACT

A lower body electrical muscle stimulation exercise system for exercising the legs of a paralyzed user which incorporates electrical stimulation of leg muscles. The device is portable, light-weight and functional. The device is placed in front of a user who is sitting in a chair. The user's legs may be placed on moveable leg supports. An electric motor rotates a bicycle crank assembly which moves the legs of a user in a back and forth bending motion. Electrical stimulation is then activated which contracts or relaxes the leg muscles. The stimulation is sequentially activated by a Master Processor and a Transcutaneous Electrical Nerve Stimulator (TENS) unit. The present invention is designed to stop the deterioration of the leg muscles and restore the functionality of the legs.

17 Claims, 5 Drawing Sheets

(56) References Cited

U.S. PATENT DOCUMENTS

| | | | |
|---|---|---|---|
| 2013/0085420 A1* | 4/2013 | Feinstein | A61N 1/0468 601/5 |
| 2014/0148736 A1* | 5/2014 | Hoffman | A61H 1/024 601/5 |
| 2017/0157396 A1* | 6/2017 | Dixon | A61N 1/36003 |

* cited by examiner

LOWER BODY ELECTRICAL MUSCLE STIMULATION EXERCISE SYSTEMS

CROSS-REFERENCE TO RELATED APPLICATION

The present application is related to and claims priority from prior provisional application Ser. No. 62/283,878, filed Sep. 15, 2015 which application is incorporated herein by reference.

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of exercise apparatuses and more specifically relates to a lower body electrical muscle stimulation exercise system.

2. Description of Related Art

Paralysis is loss of muscle function for one or more muscles. Paralysis can be accompanied by a loss of feeling (sensory loss) in the affected area if there is sensory damage as well as motor. Paralysis is most often caused by damage in the nervous system, especially the spinal cord. Other major causes are stroke, trauma with nerve injury, poliomyelitis, cerebral palsy, peripheral neuropathy, Parkinson's disease, ALS, botulism, spina bifida, multiple sclerosis, and Guillain-Barré syndrome. Countless injuries occur each year leaving many people paralyzed or handicapped condition.

Various therapy methods have been tried to assist people in maintaining muscle tone in such situations. One of these methods is to treat muscles with exercise and electrical stimulation. It has been found that treating muscles with electrical stimulation can induce functional motor responses. Several devices are used for rehabilitation of muscles. However, these devices are expensive, non-portable, and beyond the ability of a single person to use. A suitable solution is desired.

Several attempts have been made to solve the above-mentioned problems such as those found in U.S. Pub. No. 2004/0172093 to Patrick Rummerfield, U.S. Pat. No. 4,947,836 to Charles Laenger; and U.S. Pat. No. 4,724,842 to Thomas Charters. This art is representative of exercise apparatuses. However, none of the above inventions and patents, taken either singly or in combination, is seen to describe the invention as claimed.

Preferably, an exercise apparatus should provide a portable device designed for simulating and exercising leg muscles of said paralyzed patient and, yet would operate reliably and be manufactured at a modest expense. Thus, a need exists for a reliable lower body electrical muscle stimulation exercise system to avoid the above-mentioned problems.

BRIEF SUMMARY OF THE INVENTION

In view of the foregoing disadvantages inherent in the known exercise apparatus art, the present invention provides a novel exercise apparatus. The general purpose of the present invention, which will be described subsequently in greater detail is to provide a lower body electrical muscle stimulation exercise system.

A lower body electrical muscle stimulation exercise system is disclosed herein, in a preferred embodiment, comprising: a lower body electrical muscle stimulation exercise assembly having at least one leg support each including a thigh support, a calf support, a fixed leg support axle, a leg support hinge, and a plurality of leg-support-wheel-casters, a leg support axle, a wheel guide, a lower exerciser frame support, at least one caster, a wheel guide for leg supports, a middle support brace, a bicycle crank assembly having a lower-bicycle crank, and an upper-bicycle crank, a motor axle, a switch cam, and electrode switches, an electric motor, a cam support, and a rotating cam, a transcutaneous electrical nerve stimulation unit having a plurality of electrode wires, and at least one electrode gel pad, an exerciser cover, a display, a keypad, a switch, a power source, at least one electrical cord, a housing, a rotary encoder, a position encoder, and a master controller, a microcontroller, and a motor controller, a front vertical frame, a rear vertical frame, a horizontal frame, and at least one mounting bracket.

The lower body electrical muscle stimulation exercise system may comprise the lower body electrical muscle stimulation exercise assembly. The lower body electrical muscle stimulation exercise assembly may comprise the at least one leg support, the leg support axle, the wheel guide, the lower exerciser frame support, the at least one caster, the middle support brace, the bicycle crank assembly, the motor axle, the electric motor, the cam support, the rotating cam, the transcutaneous electrical nerve stimulation unit, the exerciser cover, the display, the keypad, the power source, the at least one electrical cord, the housing, the rotary encoder, the position encoder, the master controller, the front vertical frame, the rear vertical frame, the horizontal frame, and the at least one mounting bracket.

Each of the at least one leg support may comprise thigh support, the calf support, the fixed leg support axle, the leg support hinge, and the plurality of leg-support-wheel-casters. The bicycle crank assembly may comprise the lower-bicycle crank and the upper-bicycle crank. The motor axle may comprise the switch cam and the electrode reed switches.

The source of electrical stimulation is the transcutaneous electrical nerve stimulation unit. The electrical stimulation is adjustable based on preference of the user. The transcutaneous electrical nerve stimulation unit provides low voltage signals of less than 60 volts. The transcutaneous electrical nerve stimulation unit may comprise the plurality of electrode wires and the at least one electrode gel pad. The at least one electrode gel pad may comprise adhesive properties for attaching to a surface.

The master controller may comprise the microcontroller and the motor controller. The calf support may comprise a plurality of leg support casters which allow the at least one leg support to move back and forth within parameters of the wheel guide. The wheel guide directs movement of the at least one leg support and the bicycle crank assembly which rotates in a circular motion. The bicycle crank is connected to the at least one leg support and moves the leg supports in a back and forth motion which also causes the leg supports to bend upward at a knee location. The bicycle crank assembly provides motion to the at least one leg support. The housing encloses inner components of the lower body electrical muscle stimulation exercise assembly.

The lower exerciser frame support is located at a base of lower body electrical muscle stimulation exercise assembly for providing stabilization. The at least one caster is located at an end of the lower exerciser frame support allowing a user to easily roll and move the lower body electrical muscle stimulation exercise assembly providing ease of portability. The motor axle is a pivot that turns the bicycle crank assembly which provides the circular motion. The power source supplies electric power to the lower body electrical muscle stimulation exercise assembly. The power source may comprise an AC wall power supply.

The lower body electrical muscle stimulation exercise assembly is supported by an H-shaped pattern made by the front vertical frame, the rear vertical frame, and the horizontal frame. A rear of the at least one leg support is fastened to the leg support axle. A front of the at least one leg support is mounted on the plurality of leg-support-wheel-casters which allow the leg supports to move back and forth. The at least one leg support rotates and bends about an axis. The at least one leg support contours to the leg and the thigh of the user. The wheel guide keeps the leg-support-wheel-casters moving in a prescribed lane such that the at least one leg support moves straight back and forth.

The electric motor powers the lower body electrical muscle stimulation exercise assembly by giving the lower body electrical muscle stimulation exercise assembly rotational motion. The electric motor may comprise a 110-volt electric motor. The electric motor, the rotational cam, and the bicycle crank assembly are held in place by the middle support brace.

The keypad and the display are attached to a rear of the housing attached to the exerciser cover for simplicity of handling and programming by a paralyzed patient, the user. The keypad may comprise a switch. The key pad may comprise the switch having an on option and off option. The key pad may comprise patient-input means for amplitude of the electrical stimulus. The display may comprise a liquid crystal display panel.

The master controller and the transcutaneous electrical nerve stimulation unit are braced to the horizontal frame. The rotating cam turns, the rotating cam makes contact with the electrode reed switches a slower rotation causes more stimulus to be applied to legs of the patient. The at least one mounting bracket are able to be rotated such that the stimulus is applied at varying degrees allowing the stimulus to be applied to a top of thigh muscles of the patient causing the muscles to contract and pull a leg upward, as the leg begins to lower, the stimulus is applied to a bottom of the thigh muscle causing the muscle to contract and straighten the leg.

The lower body electrical muscle stimulation exercise assembly produces a leg-motion in which a distance between feet and hips of the patient increases and decreases alternately. The lower body electrical muscle stimulation exercise assembly is a portable device designed for simulating and exercising leg muscles of the paralyzed patient. The lower body electrical muscle stimulation exercise assembly is useful for exercising leg muscles of the paralyzed patient.

A method of use is also disclosed herein in including the steps of: plugging in lower body electrical muscle stimulation exercise assembly; turning on the lower body electrical muscle stimulation exercise system using a switch; entering parameters for speed of rotation and amplitude of electrical stimulus; and exercising.

The present invention holds significant improvements and serves as a lower body electrical muscle stimulation exercise system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, lower body electrical muscle stimulation exercise system, constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to an exercise apparatus and more particularly to a lower body electrical muscle stimulation exercise system as used to improve the ability for a paralyzed patient user to exercise his/her legs and prevent muscle atrophy.

Generally speaking, lower body electrical muscle stimulation exercise system is a portable exerciser having a capability of exercising legs of a paralyzer patent user.

Lower body electrical muscle stimulation exercise system comprises position encoder which determines a position of a limb being exercised. This is driven by an electric motor. The position information of the position encoder is read by the microcontroller. The microcontroller is controlled by a user interface of a display and a keypad. The microcontroller outputs signals to control both a drive motor and the transcutaneous electrical nerve stimulation unit. The transcutaneous electrical nerve stimulation unit is applied to the human user via gel pad electrodes. A variable number of gel pad electrodes may be used depending on the muscles desired to be stimulated. The user first sets the desired speed of the motor to move the limb of the human user. The user then sets the amount of stimulation desired for each pair of gel pad electrodes as well as the timing of the stimulation. The motor moves the limb of the human user and the limb would also be stimulated according to the timing determined by the user.

The present invention induces electrical stimulation in the leg muscles of a paralyzed person and combines with a rotational motion of the electric motor. This device is portable and may be placed in front of a user in a wheel chair. The user may place one's legs on the leg supports and the motor is then activated which causes a bicycle-type crank to turn and cause the legs to move back and forth in a bending motion. As the leg moves upward a momentary electrical stimulus is applied to the front of the upper thigh muscles. Thus causing the muscles to contract which raises the leg. The wheel crank moves in a rotary motion which then causes the leg to move in a downward motion. An electrical stimulus is applied to the rear of the upper thigh muscles. These muscles contract and the leg moves downward. The movement of a user's legs is similar to the motion of riding a bicycle.

The electric motor is variable allowing the speed of rotation to be adjusted depending on the use of the patient. The electrical stimulus may also be adjusted. The device is powered by an electric motor and the muscle stimulation is provided by a transcutaneous electrical nerve stimulation unit. The motor provides a rotational motion to an axle which turns a primary crank which then turns a secondary crank providing an orbital motion to the leg supports. The leg supports then moves a patients legs with a back and forth motion. As the legs move, a transcutaneous electrical nerve stimulation unit gives an electrical stimulation to the leg muscles which makes the muscles contract or relax. The combination of electrical stimulus and the manual movement of the legs will help prevent the atrophying of the legs.

The present invention produces a bicycle crank type of motion in which a patient legs rest on leg supports which causes a leg motion in which the distance between the feet and hips increases or decreases. The device provides a means for of electrical stimulation that causes the muscles to contract or relax. The source of electrical stimulation is a TENS unit.

Referring to the drawings by numerals of reference there is shown in FIGS. 1-4B, lower body electrical muscle stimulation exercise system 100 comprising: lower body electrical muscle stimulation exercise assembly 110 having at least one leg support each including thigh support 116, calf support 118, fixed leg support axle 120, leg support hinge 122, and plurality of leg-support-wheel-casters 124, wheel guide 126, lower exerciser frame support 128, at least one caster 130, middle support brace 132, bicycle crank assembly 134 having lower-bicycle crank 136, and upper-bicycle crank 138, motor axle 142, switch cam, and electrode switches 146, electric motor 148, cam support, and rotating cam 154, transcutaneous electrical nerve stimulation unit 156 having a plurality of electrode wires 158, and at least one electrode gel pad 160, exerciser cover 162, display 164, keypad 166, switch 168, power source 170, at least one electrical cord 171, housing 172, rotary encoder 174, position encoder, and master controller, microcontroller 180, and motor controller 182, front vertical frame 184, rear vertical frame 186, horizontal frame 188, and at least one mounting bracket 190.

Lower body electrical muscle stimulation exercise assembly 110 has at least one leg support each including thigh support 116, calf support 118, fixed leg support axle 120, leg support hinge 122, and plurality of leg-support-wheel-casters 124, wheel guide 126, lower exerciser frame support 128, at least one caster 130, middle support brace 132, bicycle crank assembly 134 having lower-bicycle crank 136, and upper-bicycle crank 138, motor axle 142, switch cam, and electrode switches 146, electric motor 148, cam support, and rotating cam 154, transcutaneous electrical nerve stimulation unit 156 having a plurality of electrode wires 158, and at least one electrode gel pad 160, exerciser cover 162, display 164, keypad 166, switch 168, power source 170, at least one electrical cord 171, housing 172, rotary encoder 174, position encoder, and master controller, microcontroller 180, and motor controller 182, front vertical frame 184, rear vertical frame 186, horizontal frame 188, and at least one mounting bracket 190.

Each of the at least one leg support(s) 114 comprises thigh support 116, calf support 118, fixed leg support axle 120, leg support hinge 122, and a plurality of leg-support-wheel-casters 124. The bicycle crank assembly 134 comprises lower-bicycle crank 136 and upper-bicycle crank 138. The motor axle 142 comprises switch cam and electrode reed switches 146. The transcutaneous electrical nerve stimulation unit 156 comprises plurality of electrode wires 158 and at least one electrode gel pad 160. Keypad 166 comprises switch 168. Master controller comprises microcontroller 180 and motor controller 182.

Calf support 118 comprises a plurality of leg-support-wheel-casters 124 which allow at least one leg support 114 to move back and forth within parameters of wheel guide 126. Wheel guide 126 directs movement of at least one leg support 114 and bicycle crank assembly 134 which rotates in a circular motion. Bicycle crank assembly 134 is connected to at least one leg support 114 and moves leg supports 114 in a back and forth motion which also causes leg supports 114 to bend upward at a knee location. Housing 172 encloses inner components of lower body electrical muscle stimulation exercise assembly 110. The lower exerciser frame support 128 is located at a base of lower body electrical muscle stimulation exercise assembly 110 for providing stabilization.

The at least one caster 130 is located at an end of lower exerciser frame support 128 allowing a user to easily roll and move lower body electrical muscle stimulation exercise assembly 110 providing ease of portability. Motor axle 142 is a pivot that turns bicycle crank assembly 110 which provides the circular motion. Power source 170 supplies electric power to lower body electrical muscle stimulation exercise assembly 110.

Lower body electrical muscle stimulation exercise assembly 110 is supported by an H-shaped pattern made by front vertical frame 184, rear vertical frame 186, and horizontal frame 188. A rear of at least one leg support 114 is fastened to leg support axle 120. A front of at least one leg support 114 is mounted on the a plurality of leg-support-wheel-casters 124 which allow leg supports 114 to move back and forth. Wheel guide 126 keeps leg-support-wheel-casters 124 moving in a prescribed lane such that at least one leg support 114 moves straight back and forth. The electric motor powers lower body electrical muscle stimulation exercise assembly 110 by giving lower body electrical muscle stimulation exercise assembly 110 rotational motion.

Electric motor 148, rotating cam 154, and bicycle crank assembly 110 are held in place by middle support brace 132. Keypad 166 and display are attached to a rear of housing 172 attached to the exerciser cover for simplicity of handling and programming by paralyzed patient-user 140. Master controller and transcutaneous electrical nerve stimulation unit 156 are braced to horizontal frame 188. As rotating cam turns 154, rotating cam 154 makes contact with electrode reed switches 146 a slower rotation causes more stimulus to be applied to legs of patient-user 140.

At least one mounting bracket 190 is able to be rotated such that the stimulus is applied at varying degrees allowing stimulus to be applied to a top of thigh muscles of patient-user 140 causing muscles to contract and pull leg 141 upward, as leg 141 begins to lower, stimulus is applied to a bottom of the thigh muscle causing the muscle to contract and straighten leg 141. Lower body electrical muscle stimulation exercise assembly 110 is useful for exercising leg muscles of a paralyzed patient-user 140.

Power source 170 comprises an AC wall power supply. Power supply 170 comprises batteries. Display 164 comprises a liquid crystal display panel. Electric motor 148 comprises a 110-volt electric motor. Lower body electrical muscle stimulation exercise assembly 110 produces a leg-motion in which a distance between feet and hips of patient-user 140 increases and decreases alternately. Source of electrical stimulation is the transcutaneous electrical nerve stimulation unit 156. Electrical stimulation is adjustable based on preference of patient-user 140. Transcutaneous electrical nerve stimulation unit 156 provides low voltage signals of less than 60 volts.

Bicycle crank assembly 134 provides motion to at least one leg support 114. At least one leg support 114 rotates and bends about an axis. At least one leg support 114 contours to leg 141 and thigh of patient-user 140. Key pad 166 comprises switch 168 having an on option and off option. Key pad 166 comprises patient-input means for amplitude of the electrical stimulus. At least one electrode gel pad 166 comprises adhesive properties for attaching to a surface. As such, lower body electrical muscle stimulation exercise assembly 110 is a portable device designed for simulating and exercising leg 141 muscles of paralyzed patient-user 140.

Lower body electrical muscle stimulation exercise system 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different color combinations, parts may be sold separately, etc., may be sufficient.

Figure 1:
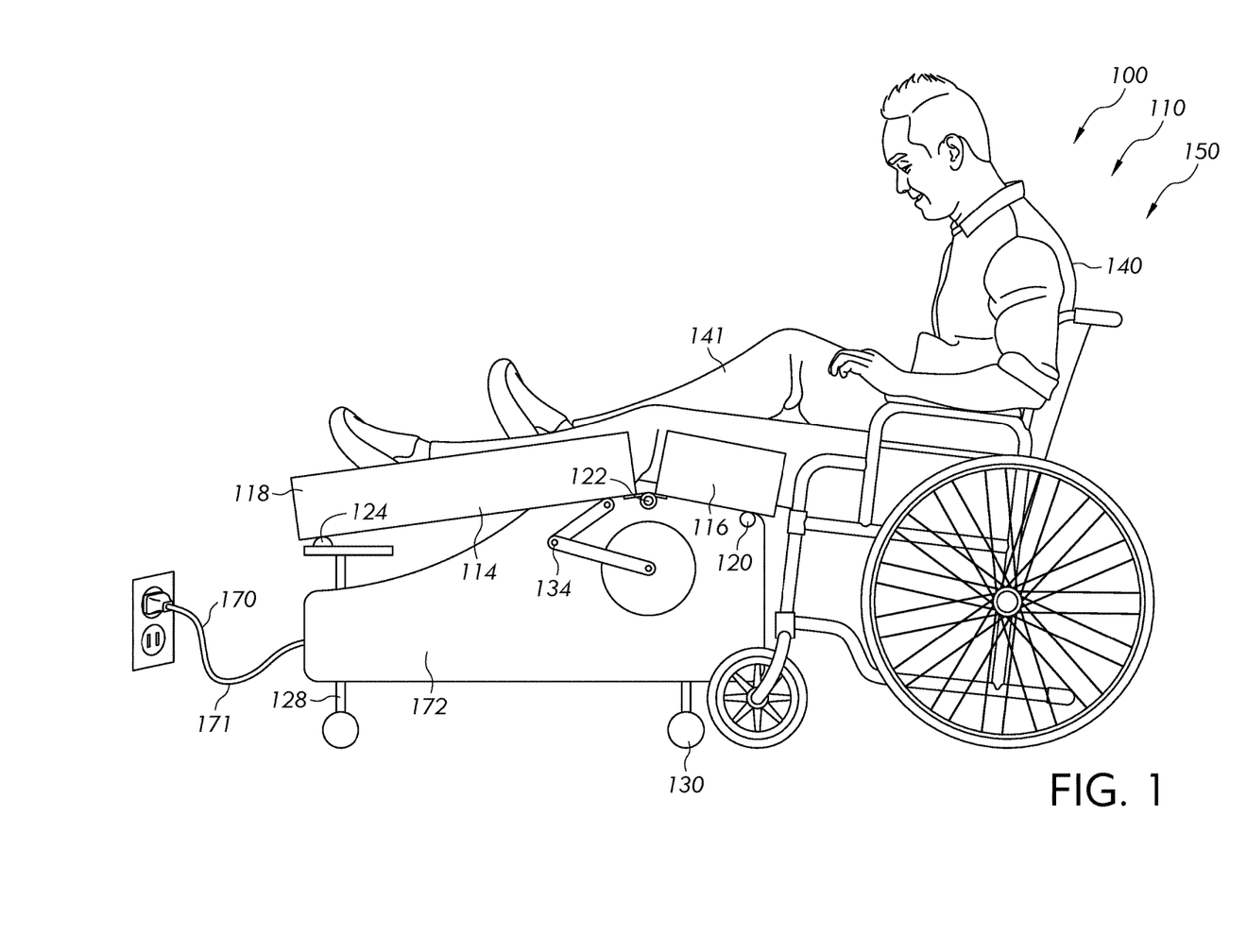
FIG. 1 shows a perspective view illustrating a lower body electrical muscle stimulation exercise system during an 'in-use' condition according to an embodiment of the present invention.
Figure 2:
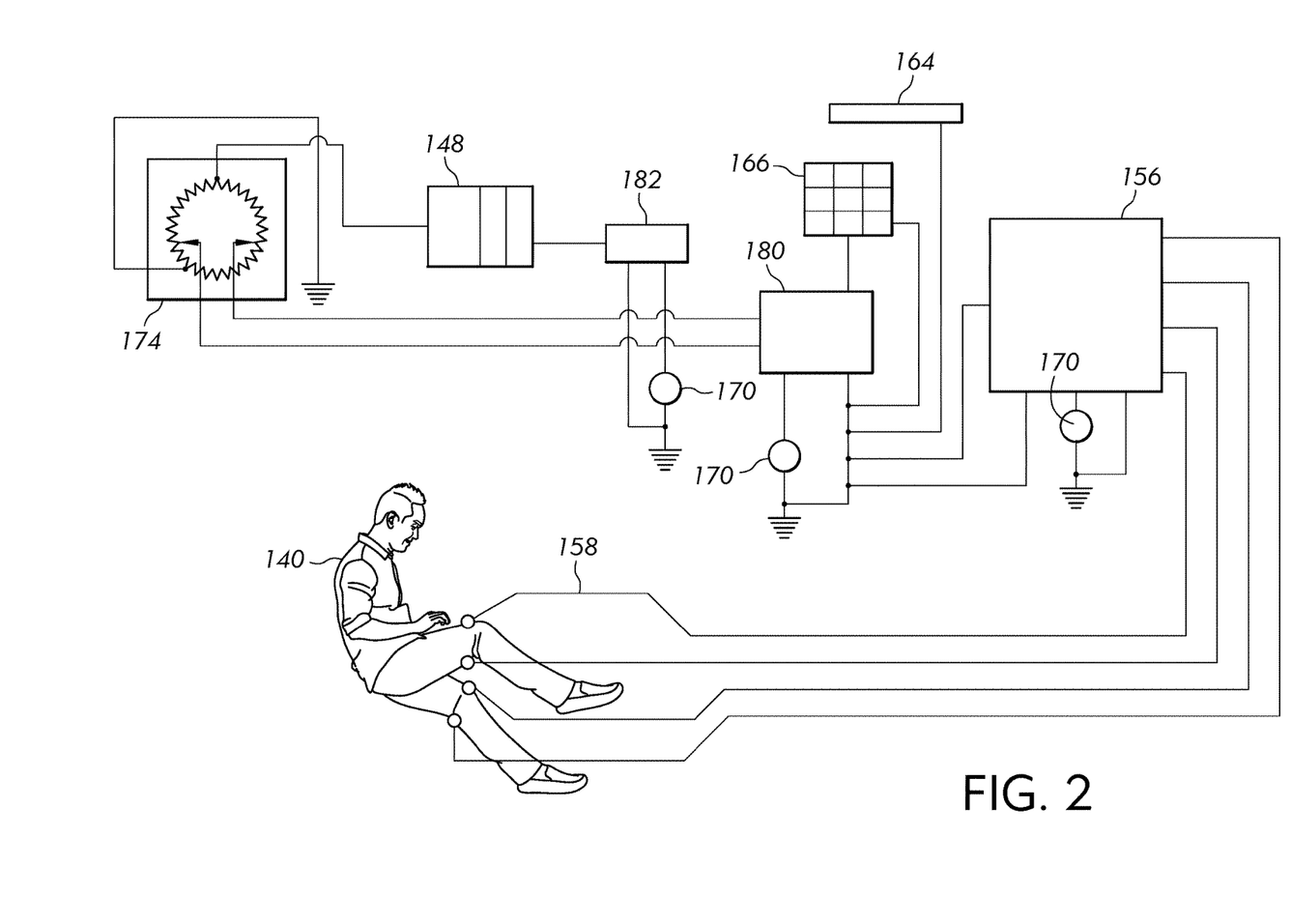
FIG. 2 is a perspective view illustrating the lower body electrical muscle stimulation exercise system comprising a lower body electrical muscle stimulation exercise assembly according to an embodiment of the present invention of FIG. 1.
Figure 3:
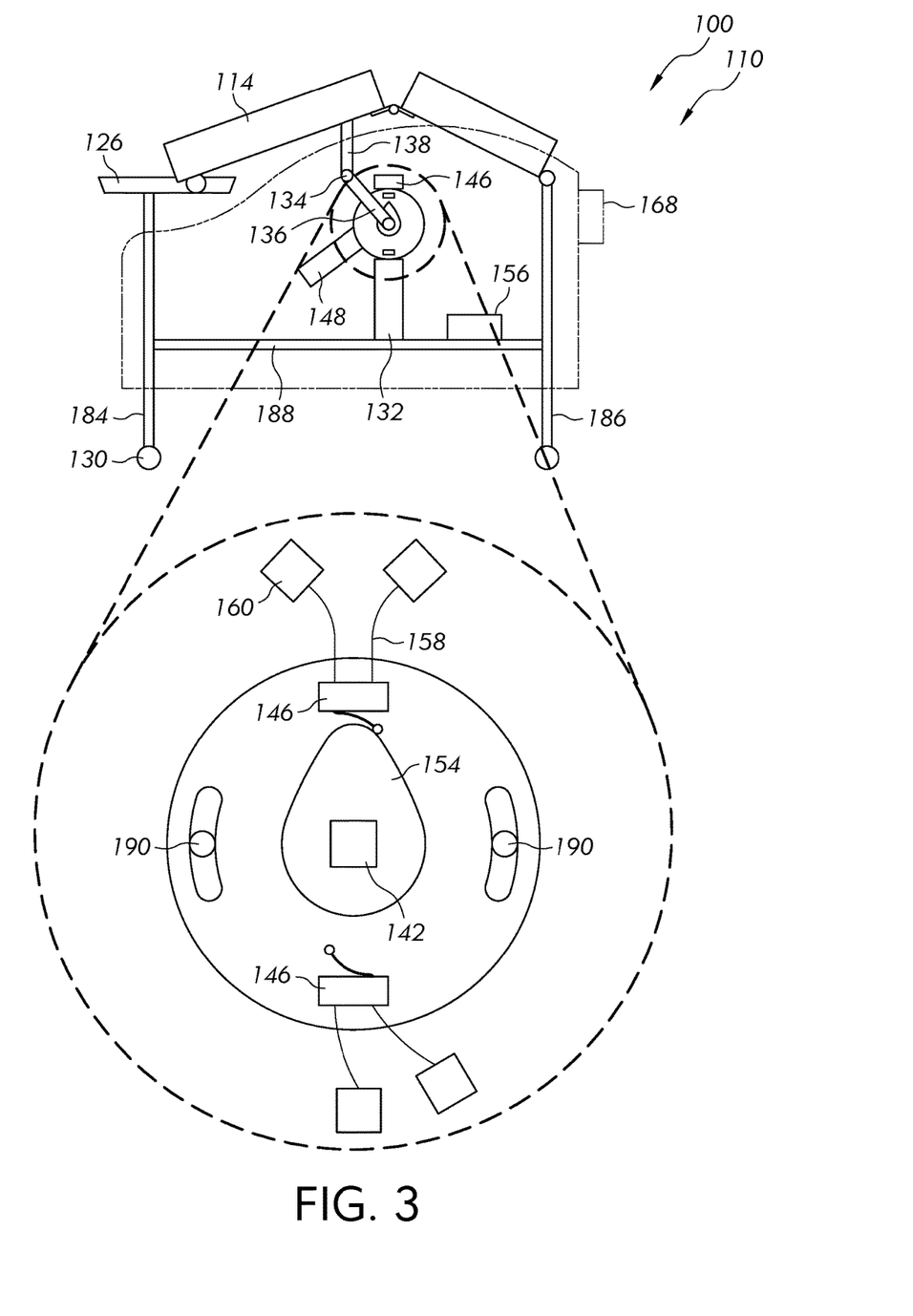
FIG. 3 is a perspective view illustrating the lower body electrical muscle stimulation exercise assembly according to an embodiment of the present invention of FIGS. 1-2.
Figure 4A:
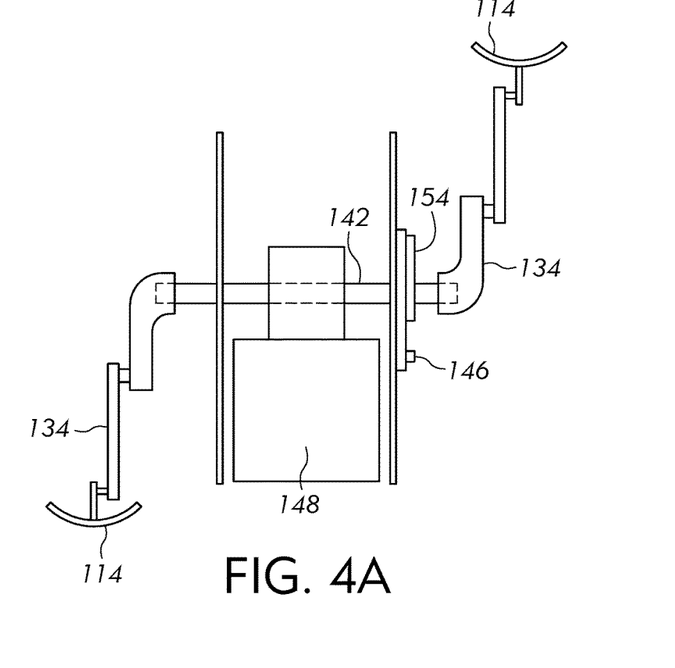
FIG. 4A is a perspective view illustrating the lower body electrical muscle stimulation exercise assembly according to an embodiment of the present invention of FIGS. 1-3.
Figure 4B:
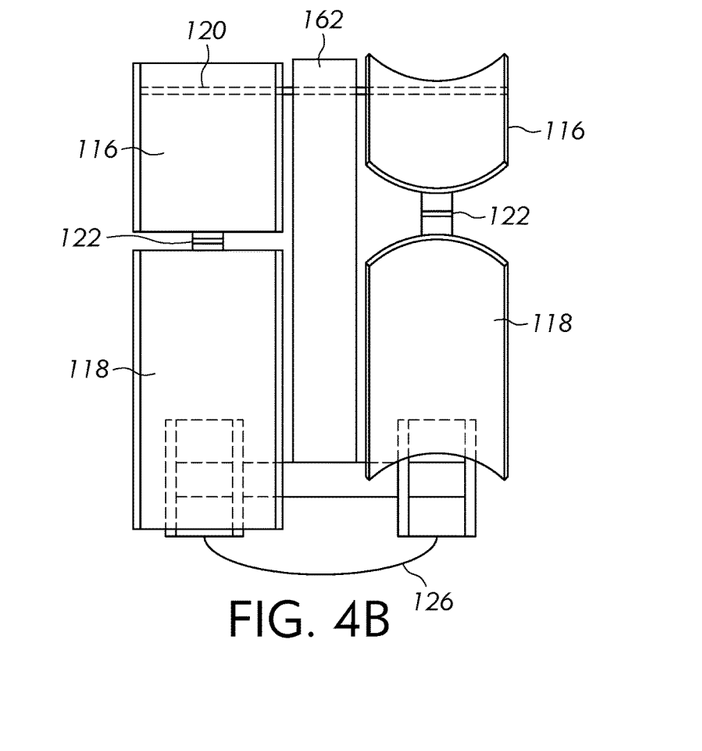
FIG. 4B is a perspective view illustrating the lower body electrical muscle stimulation exercise assembly according to an embodiment of the present invention of FIGS. 1-3.
Figure 5:
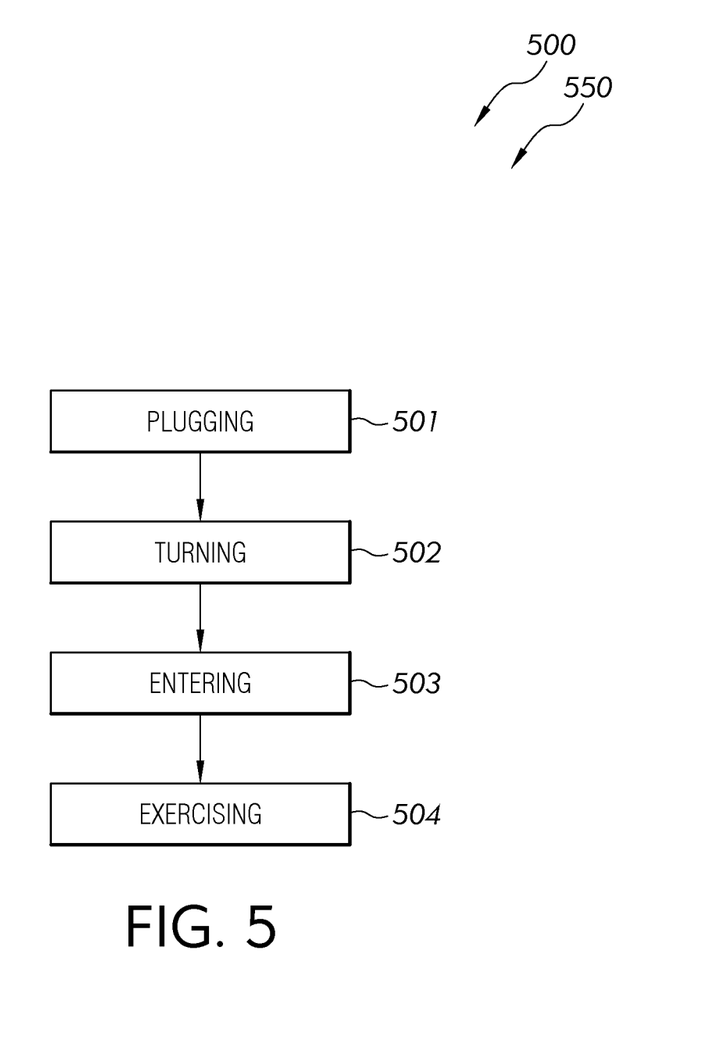
FIG. 5 is a flowchart illustrating a method of use for the lower body electrical muscle stimulation exercise system according to an embodiment of the present invention of FIGS. 1-4B.

Referring now to FIG. 5 showing flowchart 550 illustrating method of use 500 for lower body electrical muscle stimulation exercise system 100 according to an embodiment of the present invention of FIGS. 1-4B. As shown, method of use 500 may comprise the steps of: step one 501, plugging in lower body electrical muscle stimulation exercise assembly; step two 502, turning on said lower body electrical muscle stimulation exercise system using a switch; step three 503, entering parameters for speed of rotation and amplitude of electrical stimulus; and step four 504, exercising.

It should be noted that the steps described in the method of use can be carried out in many different orders according to user preference. The use of "step of" should not be interpreted as "step for", in the claims herein and is not intended to invoke the provisions of 35 U.S.C. §112, ¶6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A lower body electrical muscle stimulation exercise system comprising:
   a lower body electrical muscle stimulation exercise assembly having:
      at least one leg support each including:
         a thigh support;
         a calf support;
         a fixed leg support axle;
         a leg support hinge; and
         a plurality of leg-support-wheel-casters;
      a wheel guide;
      at least one caster;
      a middle support brace;
      a bicycle crank assembly having:
         a lower-bicycle crank; and
         an upper-bicycle crank;
      a motor axle having:
         a switch cam; and
         electrode switches;
      an electric motor;
      a cam support assembly including:
         a rotating cam;
      a transcutaneous electrical nerve stimulation unit having:
         a plurality of electrode wires; and
         at least one electrode gel pad;
      an exerciser cover;
      a display;
      a keypad having:
         a switch;
      a power source;
      at least one electrical cord;
      a housing;
      a rotary encoder;
      a position encoder; and
      a master controller having:
         a microcontroller; and
         a motor controller;
      a lower exerciser frame support having:
         a front vertical frame;
         a rear vertical frame;
         a horizontal frame; and
         at least one mounting bracket;
wherein said lower body electrical muscle stimulation exercise system comprises said lower body electrical muscle stimulation exercise assembly;
wherein said lower body electrical muscle stimulation exercise assembly comprises said at least one leg support, said wheel guide, said lower exerciser frame support, said at least one caster, said middle support brace, said bicycle crank assembly, said motor axle, said electric motor, said cam support, said rotating cam, said transcutaneous electrical nerve stimulation unit, said exerciser cover, said display, said keypad, said power source, said at least one electrical cord, said housing, said rotary encoder, said position encoder, said master controller, said front vertical frame, said rear vertical frame, said horizontal frame, and said at least one mounting bracket;

wherein each of said at least one leg support comprise said thigh support, said calf support, said fixed leg support axle, said leg support hinge, and said plurality of leg-support-wheel-casters;

wherein said bicycle crank assembly comprises said lower-bicycle crank and said upper-bicycle crank;

wherein said motor axle comprises said switch cam and said electrode switches;

wherein said transcutaneous electrical nerve stimulation unit comprises said plurality of electrode wires and said at least one electrode gel pad;

wherein said keypad comprises said switch;

wherein said master controller comprises said microcontroller and said motor controller;

wherein said calf support comprises said plurality of leg-support-wheel-casters which allow said at least one leg support to move back and forth within parameters of said wheel guide;

wherein said wheel guide directs movement of said at least one leg support and said bicycle crank assembly which rotates in a circular motion;

wherein said bicycle crank assembly is connected to said at least one leg support and moves said at least one leg support in a back and forth motion which also causes said at least one leg support to bend upward at a knee location;

wherein said housing encloses inner components of said lower body electrical muscle stimulation exercise assembly;

wherein said lower exerciser frame support is located at a base of said lower body electrical muscle stimulation exercise assembly for providing stabilization;

wherein said at least one caster is located at an end of said lower exerciser frame support allowing a user to easily roll and move said lower body electrical muscle stimulation exercise assembly providing ease of portability;

wherein said motor axle is a pivot that turns said bicycle crank assembly which provides said circular motion;

wherein said power source supplies electric power to said lower body electrical muscle stimulation exercise assembly;

wherein said lower body electrical muscle stimulation exercise assembly is supported by an h-shaped pattern made by said front vertical frame, said rear vertical frame, and said horizontal frame;

wherein a rear of said at least one leg support is fastened to said fixed leg support axle;

wherein a front of said at least one leg support is mounted on said plurality of leg-support-wheel-casters which allow said at least one leg support to move back and forth;

wherein said wheel guide keeps said plurality of leg-support-wheel-casters moving in a prescribed lane such that said at least one leg support moves straight back and forth;

wherein said electric motor powers said lower body electrical muscle stimulation exercise assembly by giving said lower body electrical muscle stimulation exercise assembly rotational motion;

wherein said electric motor, said rotating cam, and said bicycle crank assembly are held in place by said middle support brace;

wherein said keypad and said display are attached to a rear of said housing attached to said exerciser cover for simplicity of handling and programming by a paralyzed user;

wherein said master controller and said transcutaneous electrical nerve stimulation unit are braced to said horizontal frame;

wherein as said rotating cam turns, said rotating cam makes contact with said electrode switches, a slower rotation causes more stimulus to be applied to legs of said user;

wherein said at least one mounting bracket are able to be rotated such that said stimulus is applied at varying degrees allowing said stimulus to be applied to a top of thigh muscles of said user causing said thigh muscles to contract and pull a leg upward, as said leg begins to lower, said stimulus is applied to a bottom of said thigh muscles causing said thigh muscles to contract and straighten said leg; and wherein said lower body electrical muscle stimulation exercise assembly is useful for exercising leg muscles of said user.

2. The lower body electrical muscle stimulation exercise system of claim 1 wherein said power source comprises an AC wall power supply.

3. The lower body electrical muscle stimulation exercise system of claim 1 wherein said power supply comprises batteries.

4. The lower body electrical muscle stimulation exercise system of claim 1 wherein said display comprises a liquid crystal display panel.

5. The lower body electrical muscle stimulation exercise system of claim 1 wherein said electric motor comprises a 110-volt electric motor.

6. The lower body electrical muscle stimulation exercise system of claim 1 wherein said lower body electrical muscle stimulation exercise assembly is adapted to produce a leg motion in which a distance between feet and hips of said user increases and decreases alternately.

7. The lower body electrical muscle stimulation exercise system of claim 1 wherein said transcutaneous electrical nerve stimulation unit is a source of electrical stimulation and provides electrical stimulation.

8. The lower body electrical muscle stimulation exercise system of claim 7 wherein said electrical stimulation is adjustable based on preference of said user.

9. The lower body electrical muscle stimulation exercise system of claim 8 wherein said keypad is a patient-input means for control of amplitude of said electrical stimulus.

10. The lower body electrical muscle stimulation exercise system of claim 1 wherein said transcutaneous electrical nerve stimulation unit provides low voltage signals of less than 60 volts.

11. The lower body electrical muscle stimulation exercise system of claim 1 wherein said bicycle crank assembly provides motion to said at least one leg support.

12. The lower body electrical muscle stimulation exercise system of claim 1 wherein said at least one leg support rotates and bends about an axis.

13. The lower body electrical muscle stimulation exercise system of claim 1 wherein said at least one leg support is adapted to contour to said leg and said thigh of said user.

14. The lower body electrical muscle stimulation exercise system of claim 1 wherein said keypad comprises said switch having an on option and off option.

15. The lower body electrical muscle stimulation exercise system of claim 1 wherein said at least one electrode gel pad comprises adhesive properties for attaching to a surface.

16. The lower body electrical muscle stimulation exercise system of claim 1 wherein said lower body electrical muscle stimulation exercise assembly is a portable device designed for simulating and exercising leg muscles of said user.

17. A lower body electrical muscle stimulation exercise system comprising:
a lower body electrical muscle stimulation exercise assembly having:
at least one leg support each including:
a thigh support;
a calf support;
a fixed leg support axle;
a leg support hinge; and
a plurality of leg-support-wheel-casters;
a wheel guide;
at least one caster;
a middle support brace;
a bicycle crank assembly having:
a lower-bicycle crank; and
an upper-bicycle crank;
a motor axle having:
a switch cam; and
electrode switches;
an electric motor;
a cam support assembly including:
a rotating cam;
a transcutaneous electrical nerve stimulation unit having:
a plurality of electrode wires; and
at least one electrode gel pad;
an exerciser cover;
a display;
a keypad having:
a switch;
a power source;
at least one electrical cord;
a housing;
a rotary encoder;
a position encoder; and
a master controlling having:
a microcontroller; and
a motor controller;
a lower exerciser frame support having:
a front vertical frame;
a rear vertical frame;
a horizontal frame; and
at least one mounting bracket;
wherein said lower body electrical muscle stimulation exercise system comprises said lower body electrical muscle stimulation exercise assembly;
wherein said lower body electrical muscle stimulation exercise assembly comprises said at least one leg support, said fixed leg support axle, said wheel guide, said lower exerciser frame support, said at least one caster, said wheel guide for said at least one leg support, said middle support brace, said bicycle crank assembly, said motor axle, said electric motor, said cam support, said rotating cam, said transcutaneous electrical nerve stimulation unit, said exerciser cover, said display, said keypad, said power source, said at least one electrical cord, said housing, said rotary encoder, said position encoder, said master controller, said front vertical frame, said rear vertical frame, said horizontal frame, and said at least one mounting bracket;
wherein each of said at least one leg support comprise said thigh support, said calf support, said fixed leg support axle, said leg support hinge, and said plurality of leg-support-wheel-casters;
wherein said bicycle crank assembly comprises said lower-bicycle crank and said upper-bicycle crank;
wherein said motor axle comprises said switch cam and said electrode switches;
wherein said transcutaneous electrical nerve stimulation unit is a source of electrical stimulation and provides electrical stimulation;
wherein said electrical stimulation is adjustable based on preference of a user;
wherein said transcutaneous electrical nerve stimulation unit provides low voltage signals of less than 60 volts;
wherein said transcutaneous electrical nerve stimulation unit comprises said plurality of electrode wires and said at least one electrode gel pad;
wherein said at least one electrode gel pad comprises adhesive properties for attaching to a surface;
wherein said master controller comprises said microcontroller and said motor controller;
wherein said calf support comprises said plurality of leg-support-wheel-casters which allow said at least one leg support to move back and forth within parameters of said wheel guide;
wherein said wheel guide directs movement of said at least one leg support and said bicycle crank assembly which rotates in a circular motion;
wherein said bicycle crank assembly is connected to said at least one leg support and moves said at least one leg support in a back and forth motion which also causes said at least one leg support to bend upward at a knee location;
wherein said bicycle crank assembly provides motion to said at least one leg support;
wherein said housing encloses inner components of said lower body electrical muscle stimulation exercise assembly;
wherein said lower exerciser frame support is located at a base of lower body electrical muscle stimulation exercise assembly for providing stabilization;
wherein said at least one caster is located at an end of said lower exerciser frame support allowing a user to easily roll and move said lower body electrical muscle stimulation exercise assembly providing ease of portability;
wherein said motor axle is a pivot that turns said bicycle crank assembly which provides said circular motion;
wherein said power source supplies electric power to said lower body electrical muscle stimulation exercise assembly;
wherein said power source comprises an AC wall power supply;
wherein said lower body electrical muscle stimulation exercise assembly is supported by an h-shaped pattern made by said front vertical frame, said rear vertical frame, and said horizontal frame;
wherein a rear of said at least one leg support is fastened to said fixed leg support axle;
wherein a front of said at least one leg support is mounted on said plurality of leg-support-wheel-casters which allow said at least one leg support to move back and forth;
wherein said at least one leg support rotates and bends about an axis;
wherein said at least one leg support is adapted to contour to a leg and a thigh of said user;
wherein said wheel guide keeps said plurality of leg-support-wheel-casters moving in a prescribed lane such that said at least one leg support moves straight back and forth;
wherein said electric motor powers said lower body electrical muscle stimulation exercise assembly by giving said lower body electrical muscle stimulation exercise assembly rotational motion;
wherein said electric motor comprises a 110-volt electric motor;

wherein said electric motor, said rotational cam, and said bicycle crank assembly are held in place by said middle support brace;

wherein said keypad and said display are attached to a rear of said housing attached to said exerciser cover for simplicity of handling and programming by said user;

wherein said keypad comprises said switch;

wherein said keypad comprises said switch having an on option and off option;

wherein said keypad is a patient-input means for control of amplitude of said electrical stimulus;

wherein said display comprises a liquid crystal display panel;

wherein said master controller and said transcutaneous electrical nerve stimulation unit are braced to said horizontal frame;

wherein as said rotating cam turns, said rotating cam makes contact with said electrode switches, a slower rotation causes more stimulus to be applied to legs of said user;

wherein said at least one mounting bracket are able to be rotated such that said stimulus is applied at varying degrees allowing said stimulus to be applied to a top of thigh muscles of said user causing said thigh muscles to contract and pull a leg upward, as said leg begins to lower, said stimulus is applied to a bottom of said thigh muscles causing said thigh muscles to contract and straighten said leg;

wherein said lower body electrical muscle stimulation exercise assembly produces a leg-motion in which a distance between feet and hips of said patient increases and decreases alternately;

wherein said lower body electrical muscle stimulation exercise assembly is a portable device designed for simulating and exercising leg muscles of said user;

wherein said lower body electrical muscle stimulation exercise assembly is useful for exercising leg muscles of said user.

* * * * *